United States Patent
Baker, Jr.

(10) Patent No.: US 8,862,194 B2
(45) Date of Patent: Oct. 14, 2014

(54) METHOD FOR IMPROVED OXYGEN SATURATION ESTIMATION IN THE PRESENCE OF NOISE

(75) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 1857 days.

(21) Appl. No.: 12/165,256

(22) Filed: Jun. 30, 2008

(65) Prior Publication Data

US 2009/0326348 A1    Dec. 31, 2009

(51) Int. Cl.
*A61B 5/00* (2006.01)
*A61B 5/1455* (2006.01)

(52) U.S. Cl.
CPC .......... *A61B 5/14551* (2013.01); *A61B 5/7264* (2013.01)
USPC ....................................... 600/323

(58) Field of Classification Search
USPC ........................... 600/323, 330, 336
See application file for complete search history.

(56) References Cited

U.S. PATENT DOCUMENTS

| | | |
|---|---|---|
| 3,638,640 A | 2/1972 | Shaw |
| 4,063,824 A | 12/1977 | Baker et al. |
| 4,123,932 A | 11/1978 | Baker et al. |
| 4,714,341 A | 12/1987 | Hamaguri et al. |
| 4,805,623 A | 2/1989 | Jöbsis |
| 4,911,167 A | 3/1990 | Corenman et al. |
| 4,936,679 A | 6/1990 | Mersch |
| 4,972,331 A | 11/1990 | Chance |
| 5,119,815 A | 6/1992 | Chance |
| 5,122,974 A | 6/1992 | Chance |
| 5,167,230 A | 12/1992 | Chance |
| 5,297,548 A | 3/1994 | Pologe |
| 5,337,745 A | 8/1994 | Benaron |

(Continued)

FOREIGN PATENT DOCUMENTS

| | | |
|---|---|---|
| DE | 102 13 692 A1 | 10/2003 |
| JP | 5-212016 | 8/1993 |

(Continued)

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

(Continued)

*Primary Examiner* — Max Hindenburg
*Assistant Examiner* — Jonathan M Foreman
(74) *Attorney, Agent, or Firm* — Fletcher Yoder PC

(57) ABSTRACT

The present disclosure relates, according to some embodiments, to devices, systems, and methods for estimating a physiological parameter in the presence of noise. For example, the disclosure relates, in some embodiments, to devices, systems, and methods for assessing (e.g., estimating, measuring, calculating) oxygen saturation (SpO2). Methods of assessing SpO2 may include assessing a noise metric associated with motion artifact. In some embodiments, a percentage (e.g., an empirically determined percentage) of a noise metric may be simply added to the SpO2 estimate to produce a corrected SpO2 estimate. An oximetry algorithm may include, according to some embodiments, combining multiple internal SpO2 estimates and associated noise and/or signal quality metrics (e.g., using a radial basis neural network) to produce a modified (e.g., corrected) SpO2 estimate (e.g., rather than merely selecting the estimate from a finite number of candidates). A modified SpO2 estimate may include little or no movement-based error.

21 Claims, 7 Drawing Sheets

(56) References Cited

U.S. PATENT DOCUMENTS

| | | | |
|---|---|---|---|
| 5,355,880 A | 10/1994 | Thomas et al. | |
| 5,372,136 A | 12/1994 | Steuer et al. | |
| 5,385,143 A | 1/1995 | Aoyagi | |
| 5,482,036 A | 1/1996 | Diab et al. | |
| 5,485,847 A | 1/1996 | Baker, Jr. | |
| 5,499,627 A | 3/1996 | Steuer et al. | |
| 6,064,898 A | 5/2000 | Aldrich | |
| 6,083,172 A | 7/2000 | Baker, Jr. et al. | |
| 6,120,460 A | 9/2000 | Abreu | |
| 6,134,460 A | 10/2000 | Chance | |
| 6,163,715 A | 12/2000 | Larsen et al. | |
| 6,181,958 B1 | 1/2001 | Steuer et al. | |
| 6,183,414 B1 | 2/2001 | Wysor et al. | |
| 6,230,035 B1 | 5/2001 | Aoyagi et al. | |
| 6,246,894 B1 | 6/2001 | Steuer et al. | |
| 6,266,546 B1 | 7/2001 | Steuer et al. | |
| 6,312,393 B1 | 11/2001 | Abreu | |
| 6,334,065 B1 | 12/2001 | Al-Ali et al. | |
| 6,397,091 B2 | 5/2002 | Diab et al. | |
| 6,411,833 B1 | 6/2002 | Baker, Jr. et al. | |
| 6,415,236 B2 | 7/2002 | Kobayashi et al. | |
| 6,438,399 B1 | 8/2002 | Kurth | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,591,122 B2 | 7/2003 | Schmitt | |
| 6,594,512 B2 | 7/2003 | Huang | |
| 6,594,513 B1 | 7/2003 | Jobsis et al. | |
| 6,606,509 B2 | 8/2003 | Schmitt | |
| 6,615,064 B1 | 9/2003 | Aldrich | |
| 6,622,095 B2 | 9/2003 | Kobayashi et al. | |
| 6,658,277 B2 | 12/2003 | Wasserman | |
| 6,662,030 B2 | 12/2003 | Khalil et al. | |
| 6,671,526 B1 | 12/2003 | Aoyagi et al. | |
| 6,671,528 B2 | 12/2003 | Steuer et al. | |
| 6,675,031 B1 | 1/2004 | Porges et al. | |
| 6,678,543 B2 | 1/2004 | Diab et al. | |
| 6,687,519 B2 | 2/2004 | Steuer et al. | |
| 6,690,958 B1 | 2/2004 | Walker et al. | |
| 6,701,170 B2 | 3/2004 | Stetson | |
| 6,708,048 B1 | 3/2004 | Chance | |
| 6,711,424 B1 | 3/2004 | Fine et al. | |
| 6,711,425 B1 | 3/2004 | Reuss | |
| 6,714,804 B2 | 3/2004 | Al-Ali et al. | |
| 6,721,584 B2 | 4/2004 | Baker, Jr. et al. | |
| 6,785,568 B2 | 8/2004 | Chance | |
| 6,801,797 B2 | 10/2004 | Mannheimer et al. | |
| 6,801,799 B2 | 10/2004 | Mendelson | |
| 6,836,679 B2 | 12/2004 | Baker, Jr. et al. | |
| 6,873,865 B2 | 3/2005 | Steuer et al. | |
| 6,898,452 B2 | 5/2005 | Al-Ali et al. | |
| 6,949,081 B1 | 9/2005 | Chance | |
| 6,961,598 B2 | 11/2005 | Diab | |
| 6,999,904 B2 | 2/2006 | Weber et al. | |
| 7,006,856 B2 | 2/2006 | Baker, Jr. et al. | |
| 7,027,849 B2 | 4/2006 | Al-Ali | |
| 7,039,538 B2 | 5/2006 | Baker, Jr. | |
| 7,130,671 B2 | 10/2006 | Baker, Jr. et al. | |
| 7,162,288 B2 | 1/2007 | Nordstrom et al. | |
| 7,194,293 B2 | 3/2007 | Baker, Jr. | |
| 7,209,774 B2 | 4/2007 | Baker, Jr. | |
| 7,277,741 B2 | 10/2007 | Debreczeny et al. | |
| 7,302,284 B2 | 11/2007 | Baker, Jr. et al. | |
| 7,315,753 B2 | 1/2008 | Baker, Jr. et al. | |
| 7,328,053 B1 | 2/2008 | Diab et al. | |
| 7,336,983 B2 | 2/2008 | Baker, Jr. et al. | |
| 7,343,187 B2 | 3/2008 | Stetson | |
| 7,376,453 B1 | 5/2008 | Diab et al. | |
| 7,392,075 B2 | 6/2008 | Baker, Jr. | |
| 7,761,128 B2 * | 7/2010 | Al-Ali et al. | 600/323 |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2003/0236452 A1 | 12/2003 | Melker et al. | |
| 2004/0010188 A1 | 1/2004 | Wasserman | |
| 2004/0054270 A1 | 3/2004 | Pewzner et al. | |
| 2004/0059209 A1 | 3/2004 | Al-Ali et al. | |
| 2004/0059210 A1 | 3/2004 | Stetson | |
| 2004/0087836 A1 | 5/2004 | Green et al. | |
| 2004/0087846 A1 | 5/2004 | Wasserman | |
| 2004/0097797 A1 | 5/2004 | Porges et al. | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0181134 A1 | 9/2004 | Baker, Jr. et al. | |
| 2004/0230106 A1 | 11/2004 | Schmitt et al. | |
| 2005/0033129 A1 | 2/2005 | Edgar et al. | |
| 2005/0080323 A1 | 4/2005 | Kato | |
| 2005/0085735 A1 | 4/2005 | Baker, Jr. et al. | |
| 2005/0101850 A1 | 5/2005 | Parker | |
| 2005/0105554 A1 | 5/2005 | Kagan et al. | |
| 2005/0107676 A1 | 5/2005 | Acosta et al. | |
| 2005/0113656 A1 | 5/2005 | Chance | |
| 2005/0143634 A1 | 6/2005 | Baker, Jr. et al. | |
| 2005/0159646 A1 | 7/2005 | Nordstrom et al. | |
| 2005/0168722 A1 | 8/2005 | Forstner et al. | |
| 2005/0192488 A1 | 9/2005 | Bryenton et al. | |
| 2005/0197551 A1 | 9/2005 | Al-Ali et al. | |
| 2005/0197552 A1 | 9/2005 | Baker, Jr. | |
| 2005/0197579 A1 | 9/2005 | Baker, Jr. | |
| 2005/0197793 A1 | 9/2005 | Baker, Jr. et al. | |
| 2005/0203357 A1 | 9/2005 | Debreczeny et al. | |
| 2005/0209517 A1 | 9/2005 | Diab et al. | |
| 2005/0267346 A1 | 12/2005 | Faber et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0030764 A1 | 2/2006 | Porges et al. | |
| 2006/0052680 A1 | 3/2006 | Diab | |
| 2006/0058683 A1 | 3/2006 | Chance | |
| 2006/0135860 A1 | 6/2006 | Baker, Jr. et al. | |
| 2006/0161389 A1 | 7/2006 | Weber et al. | |
| 2006/0183988 A1 | 8/2006 | Baker, Jr. et al. | |
| 2006/0195280 A1 | 8/2006 | Baker, Jr. et al. | |
| 2006/0200015 A1 | 9/2006 | Baker, Jr. | |
| 2006/0217609 A1 | 9/2006 | Diab et al. | |
| 2006/0258923 A1 | 11/2006 | Al-Ali et al. | |
| 2006/0258924 A1 | 11/2006 | Al-Ali et al. | |
| 2006/0258925 A1 | 11/2006 | Al-Ali et al. | |
| 2006/0270920 A1 | 11/2006 | Al-Ali et al. | |
| 2006/0281983 A1 | 12/2006 | Al-Ali et al. | |
| 2007/0068527 A1 | 3/2007 | Baker, Jr. | |
| 2007/0073121 A1 | 3/2007 | Hoarau et al. | |
| 2007/0073125 A1 | 3/2007 | Hoarau et al. | |
| 2007/0073128 A1 | 3/2007 | Hoarau et al. | |
| 2007/0077200 A1 | 4/2007 | Baker | |
| 2007/0100220 A1 | 5/2007 | Baker, Jr. | |

(56) References Cited

U.S. PATENT DOCUMENTS

| | | |
|---|---|---|
| 2007/0106137 A1 | 5/2007 | Baker, Jr. et al. |
| 2007/0118027 A1 | 5/2007 | Baker, Jr. et al. |
| 2007/0179369 A1 | 8/2007 | Baker, Jr. |
| 2007/0208240 A1 | 9/2007 | Nordstrom et al. |
| 2007/0208242 A1 | 9/2007 | Baker, Jr. |
| 2007/0225581 A1 | 9/2007 | Diab et al. |
| 2007/0291832 A1 | 12/2007 | Diab et al. |
| 2008/0004514 A1 | 1/2008 | Diab et al. |
| 2008/0045823 A1 | 2/2008 | Diab et al. |
| 2008/0081325 A1 | 4/2008 | Mannheimer et al. |
| 2008/0255436 A1 | 10/2008 | Baker |
| 2008/0287756 A1* | 11/2008 | Lynn ............................ 600/323 |

FOREIGN PATENT DOCUMENTS

| | | |
|---|---|---|
| WO | WO 92/20273 | 11/1992 |
| WO | WO 94/03102 | 2/1994 |
| WO | WO 97/49330 | 12/1997 |
| WO | WO98/42249 | 10/1998 |
| WO | WO 01/45553 A1 | 6/2001 |
| WO | WO2006097437 A1 | 9/2006 |

OTHER PUBLICATIONS

Bongard, Frederic S., et al., "Continuous Dual Oximetry in Surgical critical care—Indications and Limitations," *Annals of Surgery*, vol. 216, No. 1, pp. 60-68 (1992).

* cited by examiner

METHOD FOR IMPROVED OXYGEN SATURATION ESTIMATION IN THE PRESENCE OF NOISE

FIELD OF THE DISCLOSURE

The present disclosure relates, in some embodiments, to devices, systems, and methods for estimating oxygen saturation (SpO2).

BACKGROUND OF THE DISCLOSURE

Pulse oximeters typically measure and display various blood flow characteristics including but not limited to the oxygen saturation of hemoglobin in arterial blood. Oximeters pass light through blood perfused tissue such as a finger or an ear, and photoelectrically sense the absorption of light in the tissue. The amount of light absorbed is then used to calculate the amount of the blood constituent (e.g., oxyliemoglobin) being measured.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption.

The optical signal through the tissue may be degraded by noise or other artifacts. One source of noise is ambient light which reaches the light detector. Another source of noise is electromagnetic coupling from other electronic instruments. Motion of the patient may also introduce noise onto the signal. For example, the contact between the detector and the skin, or the emitter and the skin, may be temporarily disrupted when motion causes either to move away from the skin. In addition, since blood is a fluid, it may respond differently than the surrounding tissue to inertial effects, thus resulting in momentary changes in volume at the point to which the oximeter probe is attached. Noise may degrade a pulse oximetry signal relied upon by a physician, without the physicians awareness.

An oximetry algorithm may include noise metrics to allow it to quantify artifacts that degrade SpO2 accuracy. These metrics may be used to reduce the impact of the artifacts on accuracy. For example, these metrics may be used to adapt multiple internal filters and to select from multiple internal SpO2 estimates. In cases with motion artifact, the noise metrics generally have a significant negative correlation to the SpO2 level for typical sensor designs. That is, increased motion artifact usually results in a negative SpO2 bias for transmission-type sensor designs, rather than simply generating zero-mean SpO2 errors.

SUMMARY

Accordingly, a need has arisen for improved noise metrics to correct negative SpO2 bias associated with artifacts (e.g., movement artifacts).

The present disclosure relates, according to some embodiments, to devices, systems, and methods for estimating a physiological parameter in the presence of noise. For example, the disclosure relates, in some embodiments, to devices, systems, and methods for assessing (e.g., estimating, measuring, calculating) oxygen saturation (SpO2). Methods of assessing SpO2 may include assessing a noise metric associated with motion artifact. In some embodiments, a percentage (e.g., an empirically determined percentage) of a noise metric may be simply added to the SpO2 estimate to produce a corrected SpO2 estimate. Indeed, by adding the percentage of the noise metric, the negative SpO2 bias may be corrected. An oximetry algorithm may include, according to some embodiments, combining multiple internal SpO2 estimates and associated noise and/or signal quality metrics (e.g., using a radial basis neural network) to produce a modified (e.g., corrected) SpO2 estimate (e.g., rather than merely selecting the estimate from a finite number of candidates). A modified SpO2 estimate may include little or no movement-based error.

One embodiment includes a device for estimating oxygen saturation in the presence of noise. The device may include a processor in communication with a radial basis neural network, wherein the processor is configured to receive optical oximetry data, process the optical oximetry data to produce at least one oxygen saturation estimate, communicate the at least one oxygen saturation estimate to the radial basis neural network, and receive a modified oxygen saturation estimate comprising less noise bias than the at least one oxygen saturation estimate from the radial basis neural network, wherein the radial basis neural network is configured to define the modified oxygen saturation estimate based at least in part on combining the at least one oxygen saturation estimate with corresponding signal quality metrics. The device may also include a display in communication with the processor, wherein the display is operable to display a representation of the modified oxygen saturation estimate.

One embodiment includes a method for estimating oxygen saturation in the presence of noise. The method may include determining a change in estimated oxygen saturation comprising calculating a difference between a first estimated oxygen saturation value at a first time and a second estimated oxygen saturation value at a second time. Additionally, the method may include determining a change in a saturation noise estimate between a first saturation noise estimate and a second saturation noise estimate, wherein the change in the saturation noise estimate attends the change in estimated oxygen saturation. Further, the method may include displaying either the first estimated oxygen saturation value or the second oxygen saturation value based at least in part on a comparison between the change in the estimated oxygen saturation and the change in the saturation noise estimate.

One embodiment includes a method for reducing affects of noise in an oxygen saturation estimate. The method may include solving a computer-implemented radial basis neural network using a training set of oxygen saturation estimates, wherein the training set of oxygen saturation estimates include a target saturation estimate from noise-filed data, a noise-perturbed saturation estimate, and metrics associated with calculating the noise-perturbed saturation estimate. Further, the method may include processing at least one test oxygen saturation estimate that is biased by noise using the computer-implemented radial basis neural network to produce a modified test oxygen saturation estimate comprising less noise bias than the at least one test oxygen saturation estimate.

One embodiment includes a method of detecting hypoxia in a subject. The method may include collecting optical oximetry data from a subject, processing the optical oximetry data to produce at least one oxygen saturation estimate, processing the at least one oxygen saturation estimate using a solved, computer-implemented radial basis neural network to produce at least one modified oxygen saturation estimate, and comparing the at least one modified oxygen saturation estimate with a hypoxia oxygen saturation threshold.

BRIEF DESCRIPTION OF THE DRAWINGS

Some embodiments of the disclosure may be understood by referring, in part, to the present disclosure and the accompanying drawings, wherein.

DETAILED DESCRIPTION

Figure 1:
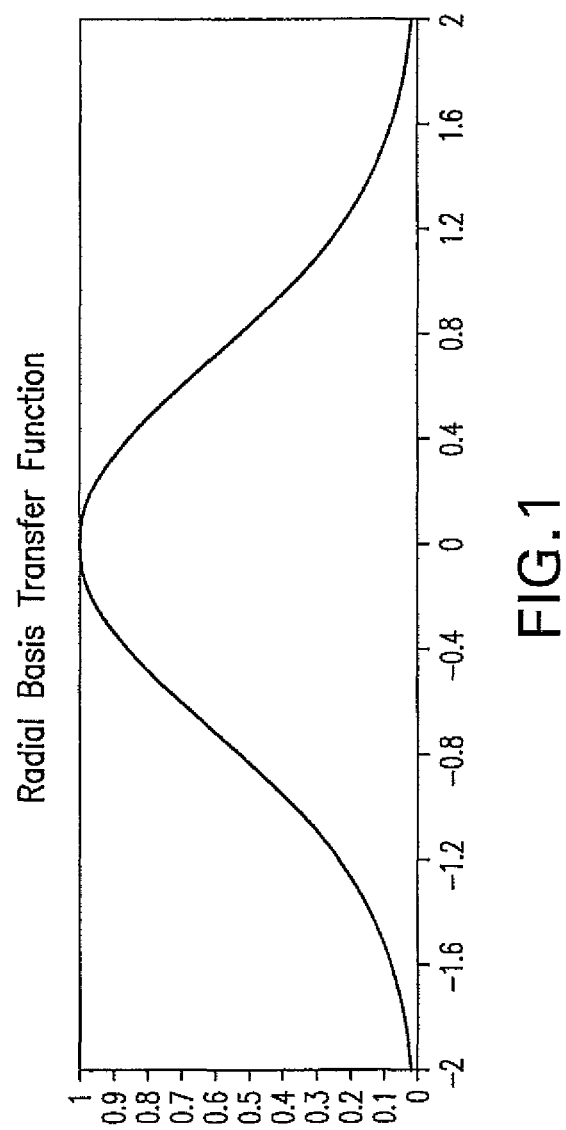
FIG. 1 illustrates a transfer function F(x) according to a specific example embodiment of the disclosure.

The present disclosure relates, in some embodiments, to devices, systems, and methods for reducing the effects of motion artifact and/or noise on a physiological parameter measurement. For example, methods according to some embodiments of the disclosure may take into account physical limitations on various physiological parameters being monitored when weighting and combining a series of samples and/or measurements. Varying weights may be assigned different measurements. Optionally, measurements may be rejected if unduly corrupt. The averaging period may be adjusted according to the reliability of the measurements in some embodiments. More specifically, a general class of filters may be employed in processing the measurements. These filters may use mathematical models which (a) describe how physiological parameters change in time and/or (b) how these parameters relate to measurement in a noisy environment. The filters may adaptively modify a set of averaging weights and/or averaging times to optimally estimate the physiological parameters.

The present disclosure relates, in some embodiments, to devices, systems, and methods for estimating oxygen saturation (SpO2). For example, a method for estimating SpO2 may comprise (a) collecting optical oximetry data from a subject, and (b) processing the data to produce at least one oxygen saturation estimate. A system, in some embodiments, may take the natural logarithm of the optical oximetry data and then bandpass filter the data to get absorption-like data. A bandpass filter may strongly attenuate data below about 0.5 Hz and/or above about 10 Hz in an attempt to remove out-of-band noise. In other words, the bandpass filter may be designed to filter out frequencies that are not due to a cardiac pulse. This filtered data may be processed through two algorithms: a rate calculator and a saturation calculator. In some embodiments, an oxygen saturation estimate may be further processed to produce a modified saturation estimate (e.g., corrected to improve accuracy). This post-processing may comprise modifying the saturation estimate using a radial basis neural network.

According to some embodiments, the present disclosure relates to methods for reducing noise effects in a system for measuring a physiological parameter. A plurality of measurements may be generated corresponding to at least one wavelength of electromagnetic energy transmitted through living tissue. Selected measurements may be compared with at least one expected measurement characteristic. A variable weight may be assigned to each of the selected measurements based on the comparison, thereby generating a plurality of differently weighted measurements for each wavelength. A first number of weighted measurements may be averaged to obtain a filtered measurement, the first number varying according to the manner in which weights are assigned to a plurality of successive weighted measurements. A plurality of filtered measurements may be generated for each wavelength. The filtered measurements for each wavelength may be then combined and calculations resulting therefrom may be adaptively filtered using variable weights based on comparing the calculations to an expected calculation. A second number of the weighted calculations may be averaged to obtain a filtered calculation, the second number varying according to the manner in which weights are assigned to a plurality of successive weighted calculations.

According to some embodiments, a method for estimating SpO2 may comprise post-processing and/or alarm handling strategies that include using a saturation noise estimate. For example, the saturation noise estimate may be used to correct the saturation estimate. Empirical data includes a number of events where the saturation estimate and saturation noise estimate are mirror images of each other. There are entire cases where the saturation estimate and saturation noise estimate are fairly well correlated. Thus, where this is true across a population, a corrected saturation estimate may be calculated as follows:

$$Sat'=Sat+k(\max-m,0)),$$

where k and m are determined empirically so as to minimize the saturation error.

In some embodiments, a saturation noise estimate may be used to determine whether a change in the saturation estimate is significant. For example, if the saturation noise estimate is high, small changes in the saturation estimate (e.g., changes that are within the range of the saturation noise estimate) may not be significant. On the other hand, if the saturation noise estimate is small, large changes in the saturation estimate (e.g., changes that exceed the saturation noise estimate) may be significant. For example, it may be desirable to show only those changes in the saturation estimate that have a 95% probability of being real. If a change in the saturation estimate is attended by a change in the saturation noise estimate from 2 points to 12 points, then the saturation estimate may be held unless the change in the saturation estimate changed by twice that delta (i.e., 2×(12 points−2 points)=20 points). It should be noted that the term "points" may refer to percent saturation, as oxygen saturation is usually displayed in increments of 1%, from 0% to 100%. In other words, a single point may correspond to 1% oxygen saturation. It may not be desirable to continue to hold a saturation estimate if the saturation noise estimate drops below what it had been when the initial decision was made to hold it. For example, if a saturation estimate changes by 15 points, but the saturation noise estimate increases from 2 points to 12 points, the saturation estimate may be held (ie., 15<20). However, if the saturation noise estimate subsequently drops to 7 points (now, 2×delta=10 points), then the 15-point change in the saturation estimate is more likely to be real. Thus, it may be desirable to discontinue holding the saturation estimate. Alternatively, an assumption may be made that, on average, a held saturation estimate becomes progressively less accurate at a rate of perhaps 0.2 saturation points per second. In such a case, if the saturation noise estimate goes from 2 points to 12 points, the saturation noise estimate may be held for up to 50 seconds (i.e., 10 points/0.2 points/second=50 seconds).

A saturation noise estimate may be used, according to some embodiments, to determine the likelihood that the saturation has crossed the saturation threshold and exceeded some sat-time integral. The sat-time integral may be defined as the difference between the oxygen saturation value and its associated alarm threshold, integrated over time, such as is described in U.S. Pat. No. 5,865,736, which is incorporated herein by reference. During motion, an alarm may only be raised when the likelihood that the alarm condition has occurred is high. For example, a saturation of 80 may mean that there is a 50% probability that the saturation is above 80 and a 50% probability that it is below 80. In the absence of motion, with a 2 point accuracy spec, the probability that that saturation estimate of 80 is below an alarm threshold of 85 is virtually 100%. But if the saturation noise estimate is 5 points, then that saturation is only one standard deviation below the threshold of 85. There is about an 84 percent probability that the saturation is below the threshold and a 16 percent probability that it is above the threshold. So, a sat-time integral may be incremented only about 68 percent (i.e., the difference between 84% and 16%) as much as in the no motion case. The noisier the saturation estimate becomes, and the closer the saturation estimate gets to the alarm threshold, the slower this alarm integral may be incremented. The alarm integral may be decremented when the saturation estimate goes above the threshold, as this may indicate a greater probability that the physiological saturation is above rather than below the alarm threshold. Furthermore, the alarm integral may be set to zero when the saturation value indicates a very high probability that the physiological saturation is above the alarm threshold (i.e. the difference between the saturation value and the alarm threshold is more than one or two times the estimate of saturation accuracy derived from one or more signal quality or noise metrics indicative of saturation accuracy).

A radial basis neural network may be used for saturation estimation, according to some embodiments. A radial basis network may be a computer-implemented, single-hidden-layer network with n unique inputs, m nodes in the hidden layer, and a single linear node in the output layer. A unique feature of a radial basis network, in some embodiments, may be the equation used by its hidden nodes. Each node (a) may receive 1 inputs, (b) may have n associated weights, and (c) may have a single bias. The equation for a node's output may be:

$$y = F(b * \text{distance}(x_1 \ldots x_n, w_1 \ldots w_n)),$$

where $x_1 \ldots x_n$ denotes the inputs,
$w_1 \ldots w_n$ denotes the weights,
b is the bias,
distance ( ) is the distance between the x and w vectors in an n-dimensional space, and $F(x) = e^{-x^2}$.

In some embodiments, a transfer function F(x) may only have a high output when its input is near zero. This is shown in FIG. 1. Therefore, the output of each radial basis neuron may be a function of how close $x_1 \ldots w_n$ is to the ideal inputs $w_1 \ldots w_n$, and the size of the region within which the neuron will output a high value (>0.5) may be proportional to b. The output of a radial basis network, therefore, may be a function of how close $x_1 \ldots x_n$ is to the weights for each hidden neuron. Matrix-based methods for solving (determining) the weights for radial basis networks are known to those skilled in the art of signal processing, and are implemented in commonly used signal processing software, such as MATLAB®. A radial-basis neural network with the previously determined weights may then be implemented in a system or apparatus embodying the invention.

Depending on the desired behavior, one skilled in the art of signal processing may define the value of b, thus controlling how much overlap there will be between the areas in the input space that each neuron is sensitive to. More overlap may be chosen to maximize coverage of the input space with a small network. Less overlap may be chosen if the neural net needed to respond very differently within narrow regions of the input space.

The ability to solve the weights for a radial basis neural network may pose an advantage over designs that apply some other types of neural networks to the same problem (i.e. accurate estimation of oxygen saturation). For example training a backpropagation network may undesirably require that its initial weights be initialized to random values, followed by iterative training. Consequently, the weights may converge to very different values in different training sessions on the same data, and these different values may significantly impact the performance of the neural net. In contrast a radial basis neural network presented with the same training data will always have the same weights determined, making its behavior repeatable.

An engineer skilled in the art of signal processing, in some embodiments, may observe the weights of each hidden neuron to determine the region of data to which a neuron is sensitive. A backpropagation network, in some embodiments, may require a monotonic transfer function that causes a neuron's output to be high over one half of the input space, low in the other half, and changing rapidly over limited region near the boundary. Thus, in some embodiments, a radial basis network may be desirable for input spaces containing many local peaks and a backpropagation network may be desirable for inputs containing many edges.

In some embodiments, a radial basis neural network may receive an input vector that is well outside of the network's training set. If this circumstance is not otherwise addressed, the output of all the hidden nodes may be virtually zero, and the output layer may output whatever its default value (bias) is. However, where an outlying data set is identified (e.g., by a skilled engineer), an additional node centered on this data may be specified and added to the hidden layer. This outlying data may then be added to the original training set. The output layer, which is always linear, may then be re-solved for the expanded training set, without having to redefine the rest of the hidden layer.

The present disclosure relates, according to some embodiments, to devices, systems, and methods for detecting oxygen saturation that crosses a threshold and/or falls within a range. For example, a method may comprise initiating or ending an alarm when an oxygen saturation estimate is below a threshold (e.g., below about 80%) or above a threshold (e.g., above about 95%). A method may comprise initiating or ending an alarm when an oxygen saturation estimate is within a selected and/or desired range. An alarm may include any type of alert that may be perceived by a human and/or a machine including, for example, a visible alert, an audible alert, and/or a tactile alert. Non-limiting examples of a visible alert include the appearance or change in appearance of text or an icon on a display and/or a blinking light (e.g., a red light). Non-limiting examples of an audible alert include an intermittent and/or continuous tone and/or playback of a recorded warning message. Non-limiting examples of a tactile alert include vibration or other movement of an object.

Embodiments of the present invention may facilitate calculation of corrected saturation values when only a single saturation value is available along with associated signal quality metrics. Further, when multiple saturation estimates and associated signal quality metrics are combined, a corrected saturation value calculated in accordance with present embodiments may not have a value between the multiple saturation estimates. Indeed, present embodiments may result in extrapolation as well as interpolation. It should be noted that in accordance with present embodiments, the combining of saturation values and associated metrics to reduce bias may be specific to a sensor model or design. For example, combination for a reflectance sensor may differ from combination for a transmission sensor.

Some specific example embodiments of the disclosure may be illustrated by one or more of the examples provided herein.

EXAMPLE 1

Breathdown Procedure

Desaturation (hypoxia) was induced by reducing the amount of oxygen in the breathing gas delivered to the subject. Normoxia (resaturation) was restored by reverting to the original breathing gas mixture. Oxygen saturation was assessed on a moving and a non-moving hand.

Five desaturations and resaturations were caused in quick succession. Simultaneous data was collected from the four fingers of the moving hand and from one finger of the non-moving hand. The non-motion saturations were concatenated from each finger of the non-moving hand to form a target vector containing twenty desaturations (FIG. 2), each of which has a minima below 80 percent. The saturations computed from the moving hand by a prior-art algorithm or an algorithm embodying the present invention may likewise be concatenated (FIGS. 3-6) to form a test set. Thus, an ideal algorithm should report twenty desaturations below 80 percent on both the non-motion and motion data.

EXAMPLE 2

Prior Art Algorithm with Pulse-Synchronous Ensemble Averaging

Figure 3:
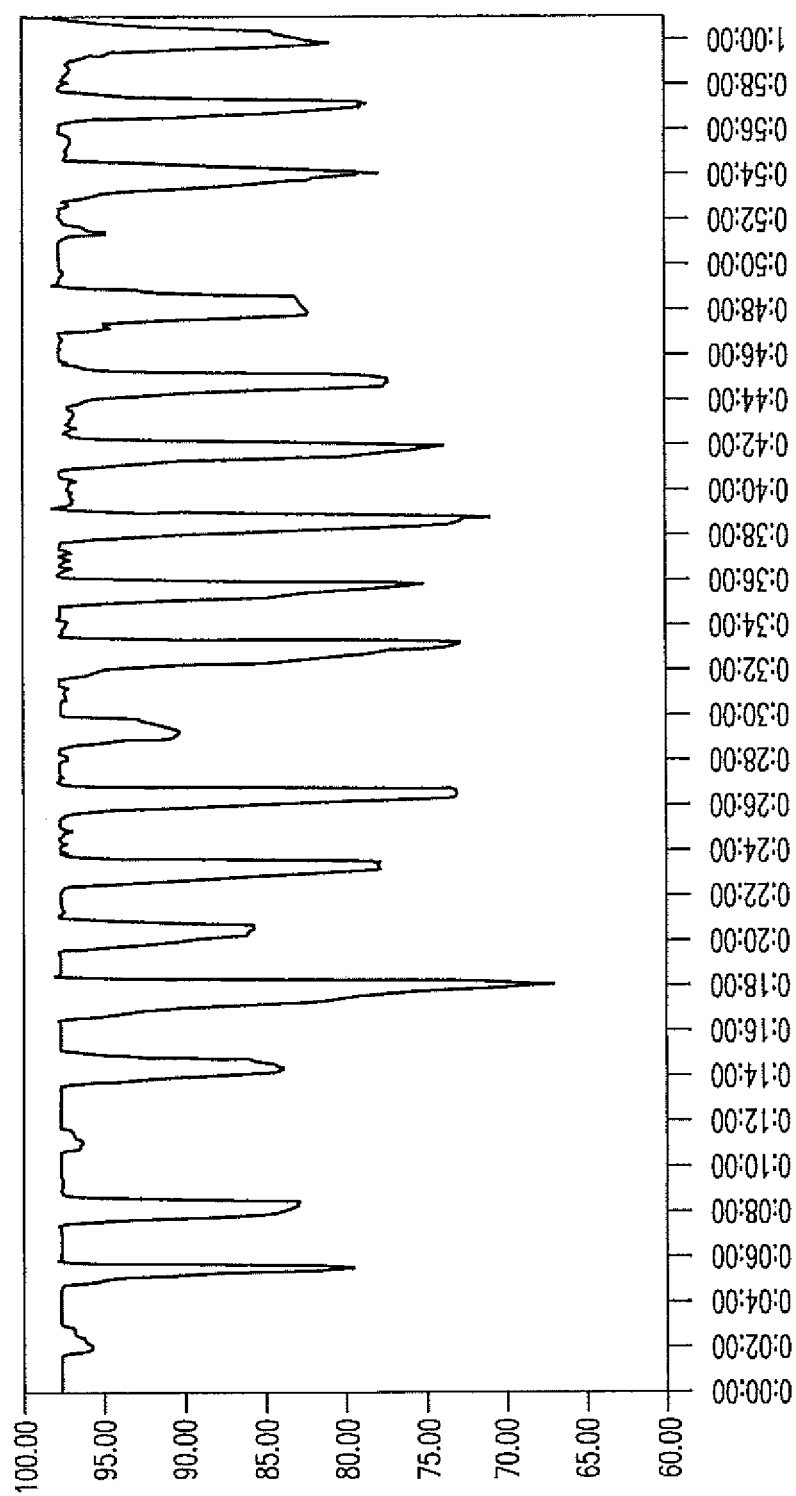
FIG. 3 illustrates oxygen saturation from moving fingers as a function of time using a prior art algorithm.
Figure 4:
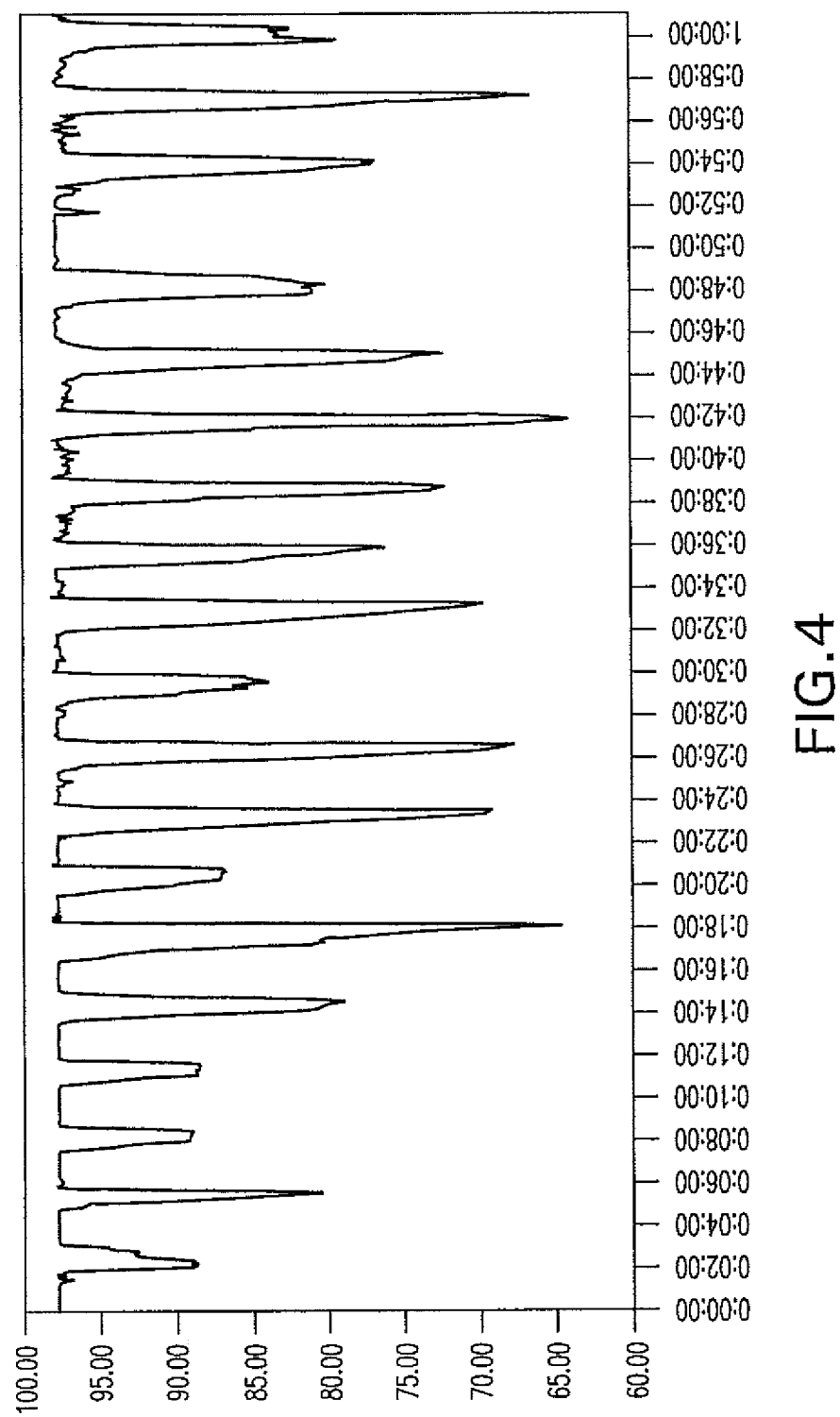
FIG. 4 illustrates oxygen saturation (SpO2) from moving fingers as a function of time using a prior art algorithm.

A prior art algorithm that computes saturation with and without pulse-synchronous ensemble averaging was tested. FIG. 3 shows the non-pulse-synchronous ensemble averaging saturation computed using the data concatenated from the four moving fingers. Saturations below 80 are calculated (detected) for only 11 of the 20 desaturations. FIG. 4 shows the pulse-synchronous ensemble averaging saturation computed using the same motion data. Saturations below 80 are calculated for only 12 of the 20 desaturations. Different desaturations were missed by the two saturation estimates.

In addition to these two saturation estimates, the same prior art algorithm also computes two associated error and "saturation age" estimates, wherein each "error" estimate quantifies the degree to which processed two-wavelength ephotoplethysmographs used to calculate a given saturation estimate are not correlated, and each "saturation age" estimate quantifies the cumulative filtering (i.e. averaging occurring in each of multiple filtering steps) used in the calculation of a given saturation estimate. One of the "saturation age" estimates is highly correlated with its corresponding error estimates, but the other is not. It has been observed that these age or error estimates are sometimes mirror images of the saturation trace. Therefore, the prior art algorithm computes five semi-independent inputs that are correlated to saturations: 2 saturations, 2 error estimates, and 2 rates.

EXAMPLE 3

A Radial Basis Network

Figure 5:
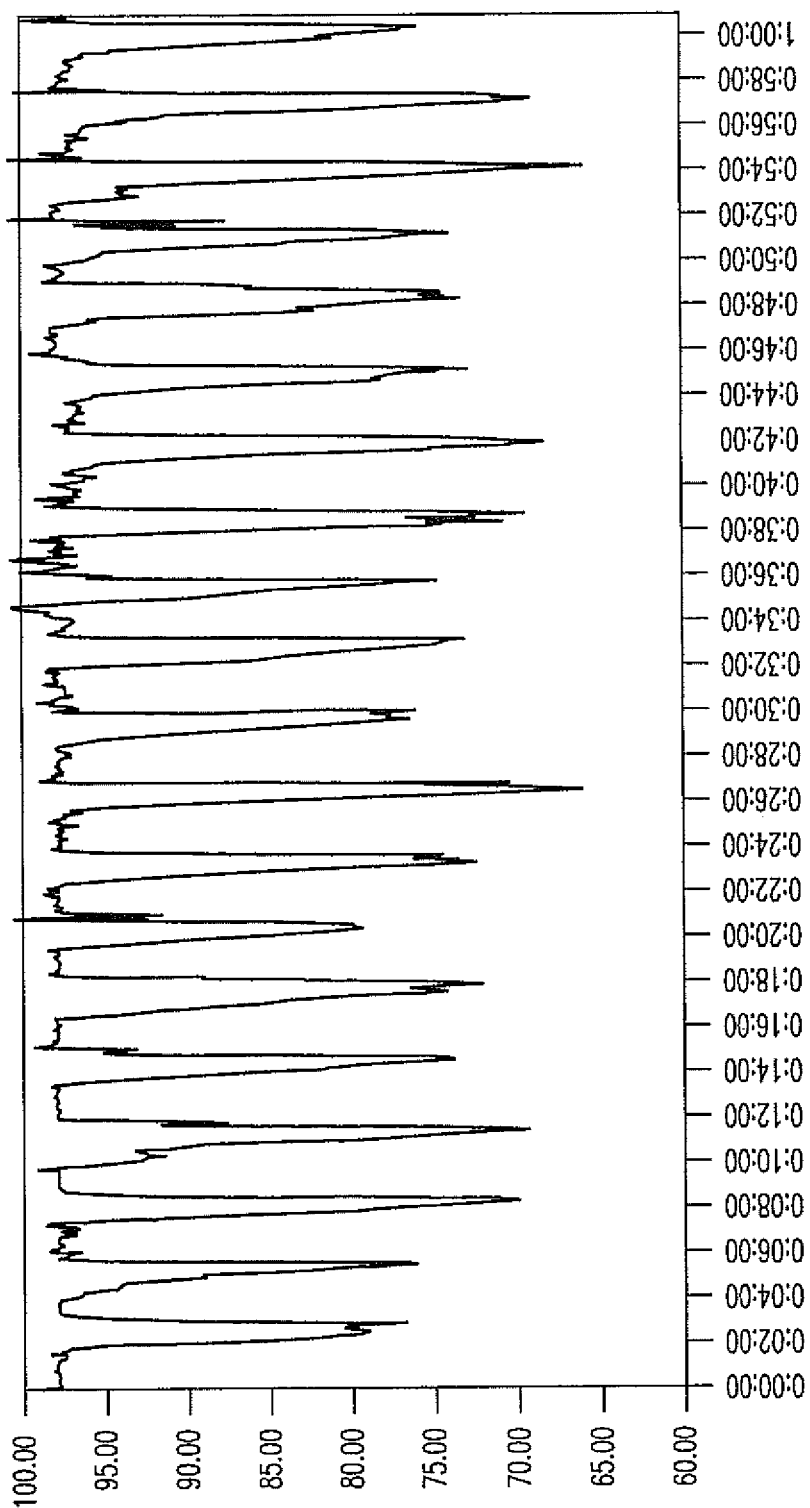
FIG. 5 illustrates oxygen saturation from moving fingers as a function of time using an algorithm according to a specific example embodiment of the disclosure.

A Radial Basis network with 30 hidden neurons was solved for this training set of 5 inputs×20 desaturation events, wherein the solving comprised determining the set of weights that minimizes the squared difference between the output of the Radial Basis neural net and the non-motion saturation estimate. The output is shown in FIG. 5.

Figure 6:
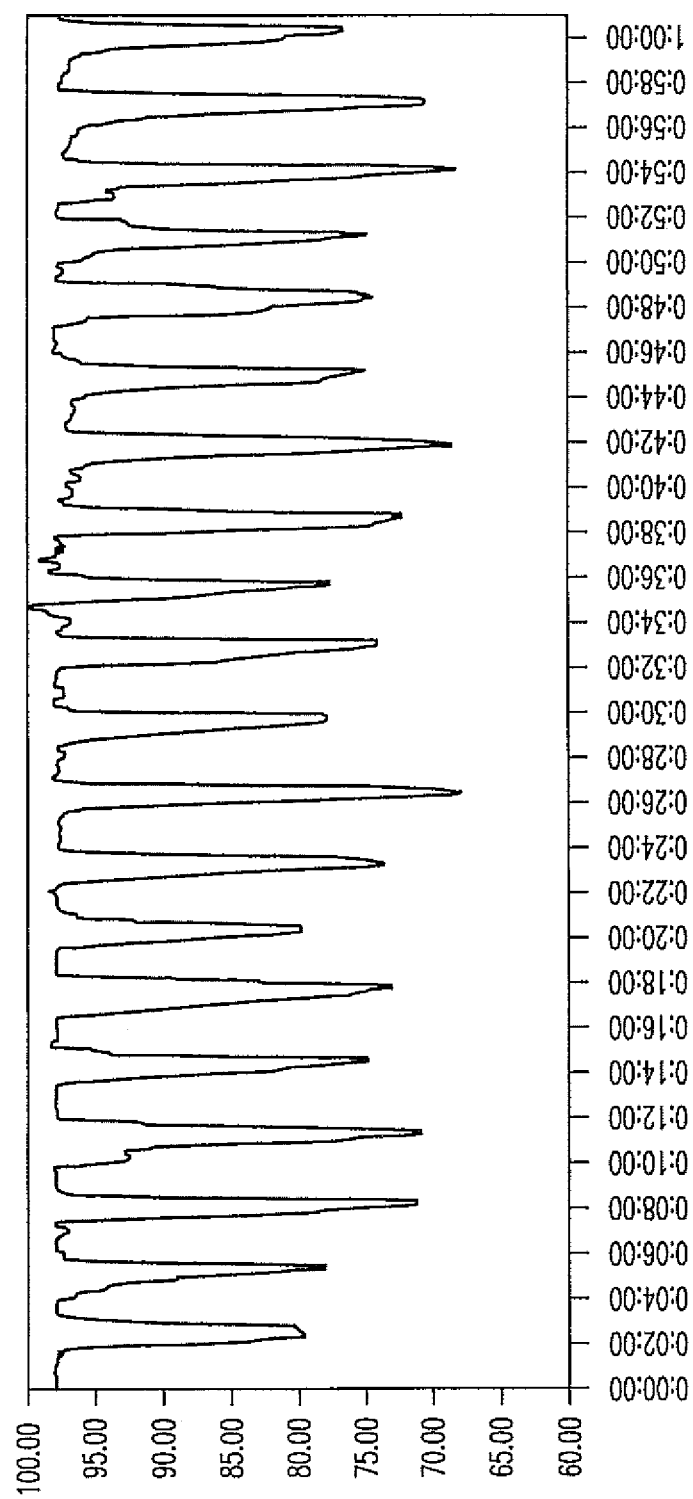
FIG. 6 illustrates oxygen saturation from moving fingers as a function of time using an algorithm according to a specific example embodiment of the disclosure.

Although the tracing in FIG. 5 contains some short-term noise, the network successfully estimated all 20 desaturations below 80. FIG. 6 shows the output of the neural net after further processing by a 20-second median filter to mitigate this noise.

Figure 2:
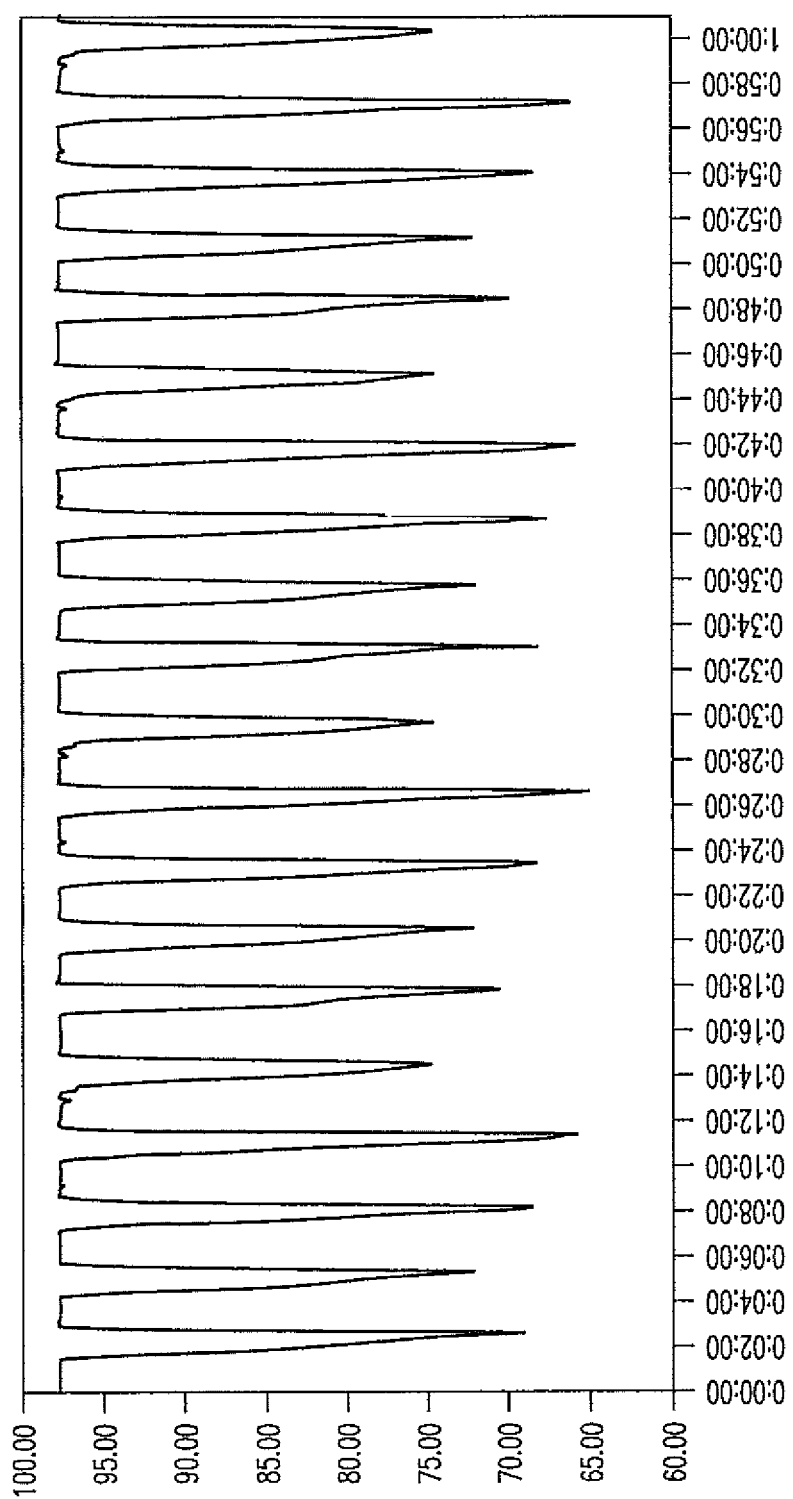
FIG. 2 illustrates oxygen saturation in a non-moving finger as a function of time using an example algorithm.

FIGS. 3 and 4 show two estimates of oxygen saturation calculated with different signal processing, each of which demonstrate unique perturbations due to motion artifact. As the text describes, each trace of oxygen saturations is associated with metrics unique to that trace. FIG. 5 demonstrates that by combining multiple estimates of oxygen saturation, such as those shown in FIGS. 3 and 4, and signal quality metrics uniquely associated with each of the multiple estimates, that embodiments of the present invention may produce a corrected saturation estimate that is significantly more accurate than either of the input saturations by itself. This is apparent when the trace in FIG. 2 is compared with the traces represented in FIGS. 3-5.

Figure 7:
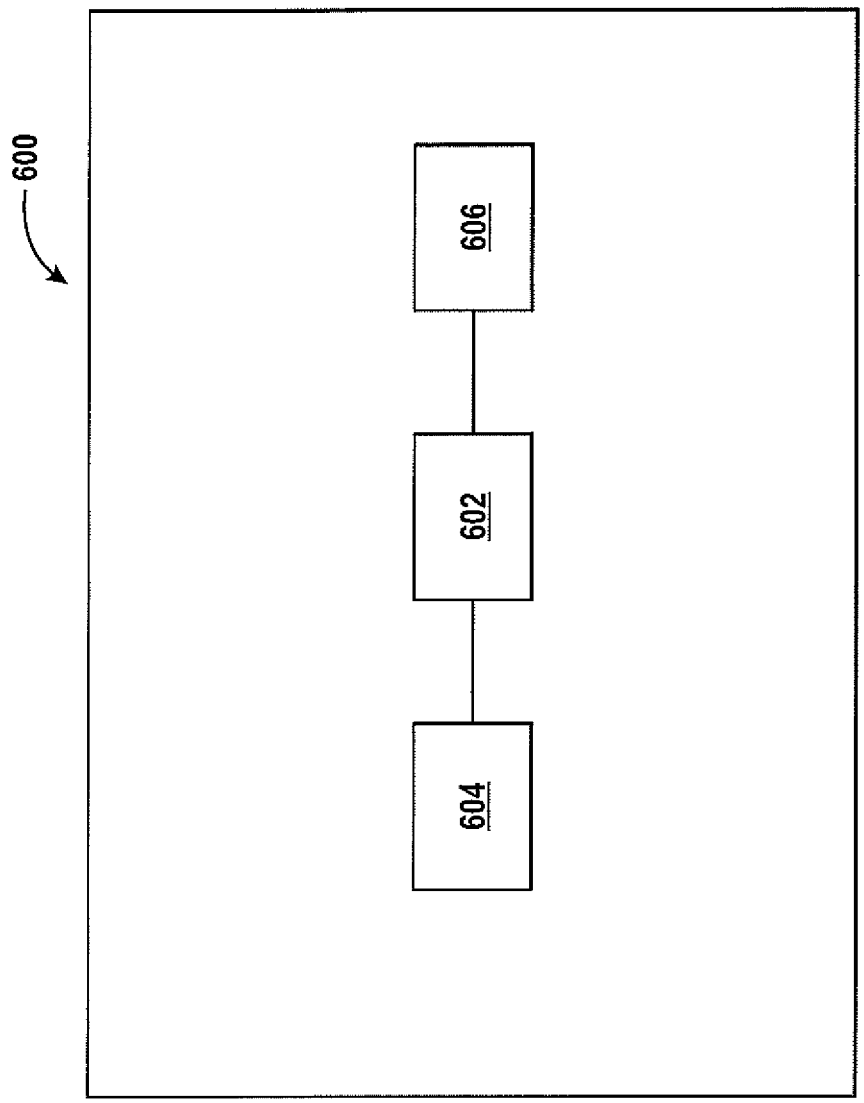
FIG. 7 is a block diagram of a device or system for estimating oxygen saturation in the presence of motion artifact.

FIG. 7 is a block diagram of a device or system for estimating oxygen saturation in the presence of motion artifact. The system is generally indicated by reference number 600. The system 600 (e.g., a computer) includes a processor 602 (e.g., a microprocessor) and a radial basis neural network 604 in communication with one another. The system 600 also includes a display 606 in communication with the processor 602. The radial basis neural network 602 may include a single-hidden-layer network and may be computer-implemented. Indeed, the radial basis neural network 604 may be stored within a memory component of the processor 602.

The processor 602 may be configured to receive optical oximetry data from a patient or from another source (e.g., a database). Further, the processor 602 may be configured to process the optical oximetry data to produce at least one oxygen saturation estimate. Once the processor 602 has produced the at least one oxygen saturation estimate, the processor 602 may be configured to communicate the at least one oxygen saturation estimate to the radial basis neural network 604. The radial basis neural network 604 may be configured to modify the oxygen saturation estimate received from the processor 602 to reduce bias caused by motion artifact. For example, the radial basis neural network 604 may be configured to define a modified oxygen saturation estimate based on combining the at least one oxygen saturation estimate received from the processor 602 with one or more additional oxygen saturation estimates and corresponding signal quality metrics to reduce motion artifact bias. Once the modified oxygen saturation estimate has been established by the radial basis neural network 604, the radial basis neural network 604 may be configured to communicate the modified oxygen saturation estimate to the processor 602, which may be configured to present a representation of the modified oxygen saturation estimate on the display 606, which may be communicatively coupled with the processor 602.

As will be understood by those skilled in the art who have the benefit of the instant disclosure, other equivalent or alternative compositions, devices, methods, and systems for estimating oxygen saturation can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, a device and/or system may include a single computer-implemented network per subject (e.g., patient) or a single computer-implemented network that serves two or more subjects. In addition, the size of a device and/or system may be scaled up or down to suit the needs and/or desires of a practitioner. Also, where ranges have been provided, the disclosed endpoints may be treated as exact and/or approximations as desired or demanded by the particular embodiment. In addition, it may be desirable in some embodiments to mix and match range endpoints. All or a portion of an oxygen saturation device and/or system may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

What is claimed is:

1. A method for estimating oxygen saturation in the presence of noise, the method comprising:
    determining a change in estimated oxygen saturation comprising calculating a difference between a first estimated oxygen saturation value at a first time and a second estimated oxygen saturation value at a second time;
    determining a change in a saturation noise estimate between a first saturation noise estimate at the first time and a second saturation noise estimate at the second time, wherein the change in the saturation noise estimate attends the change in estimated oxygen saturation;
    selecting either the first estimated oxygen saturation value or the second estimated oxygen saturation value based at least in part on a comparison between the change in the estimated oxygen saturation and the change in the saturation noise estimate; and
    displaying the selected estimated oxygen saturation value.

2. The method of claim 1, wherein the comparison between the change in the estimated oxygen saturation and the change in the saturation noise estimate comprises determining whether the change in the estimated oxygen saturation is at least a certain percentage larger than the change in the saturation noise estimate.

3. The method of claim 1, comprising initiating an alarm if the selected estimated oxygen saturation value exceeds an alarm threshold.

4. The method of claim 1, comprising processing the selected oxygen saturation estimate value using a radial basis neural network to produce a modified oxygen saturation estimate.

5. A system for estimating oxygen saturation in the presence of noise, comprising:
    a processor configured to:
        determine a change in estimated oxygen saturation comprising calculating a difference between a first estimated oxygen saturation value at a first time and a second estimated oxygen saturation value at a second time;
        determine a change in a saturation noise estimate between a first saturation noise estimate at the first time and a second saturation noise estimate at the second time, wherein the change in the saturation noise estimate attends the change in estimated oxygen saturation;
        select either the first estimated oxygen saturation value or the second estimated oxygen saturation value based at least in part on a comparison between the change in the estimated oxygen saturation and the change in the saturation noise estimate; and
    a display configured to display the selected estimated oxygen saturation value.

6. The system of claim 5, wherein the comparison between the change in the estimated oxygen saturation and the change in the saturation noise estimate comprises determining whether the change in the estimated oxygen saturation is at least a certain percentage larger than the change in the saturation noise estimate.

7. The system of claim 5, wherein the processor is configured to process the selected oxygen saturation estimate value using a radial basis neural network to produce a modified oxygen saturation estimate.

8. A method for estimating oxygen saturation in the presence of noise, the method comprising:
    determining a change in estimated oxygen saturation comprising calculating a difference between a first estimated oxygen saturation value at a first time and a second estimated oxygen saturation value at a second time;
    determining a change in a saturation noise estimate between a first saturation noise estimate and a second saturation noise estimate, wherein the change in the saturation noise estimate attends the change in estimated oxygen saturation;
    selecting either the first estimated oxygen saturation value or the second estimated oxygen saturation value based at least in part on a comparison between the change in the estimated oxygen saturation and the change in the saturation noise estimate, wherein the comparison between the change in the estimated oxygen saturation and the change in the saturation noise estimate comprises determining whether the change in the estimated oxygen saturation is at least a certain percentage larger than the change in the saturation noise estimate; and
    displaying the selected estimated oxygen saturation value.

9. The method of claim 8, comprising processing the selected oxygen saturation estimate value using a radial basis neural network to produce a modified oxygen saturation estimate.

10. The method of claim 8, wherein the comparison between the change in the estimated oxygen saturation and the change in the saturation noise estimate comprises determining whether the change in the estimated oxygen saturation is at least one hundred percent larger than the change in the saturation noise estimate.

11. The method of claim 10, comprising selecting the first estimated oxygen saturation value if the change in the estimated oxygen saturation is less than one hundred percent larger than the change in the saturation noise estimate.

12. The method of claim 10, comprising selecting the second estimated oxygen saturation value if the change in the estimated oxygen saturation is equal to or greater than one hundred percent larger than the change in the saturation noise estimate.

13. A method for estimating oxygen saturation in the presence of noise, the method comprising:
    determining a change in estimated oxygen saturation comprising calculating a difference between a first estimated oxygen saturation value at a first time and a second estimated oxygen saturation value at a second time;

determining a change in a saturation noise estimate between a first saturation noise estimate and a second saturation noise estimate, wherein the change in the saturation noise estimate attends the change in estimated oxygen saturation;

selecting either the first estimated oxygen saturation value or the second estimated oxygen saturation value based at least in part on a comparison between the change in the estimated oxygen saturation and the change in the saturation noise estimate;

processing the selected oxygen saturation estimate value using a radial basis neural network to produce a modified oxygen saturation estimate; and displaying the modified oxygen saturation estimate.

14. The method of claim 13, wherein the comparison between the change in the estimated oxygen saturation and the change in the saturation noise estimate comprises determining whether the change in the estimated oxygen saturation is at least 100 percent larger than the change in the saturation noise estimate.

15. The method of claim 13, wherein displaying the selected estimated oxygen saturation value comprises displaying the modified oxygen saturation estimate.

16. The method of claim 13, wherein the radial basis neural network comprises a single-hidden-layer network.

17. The method of claim 16, wherein the single-hidden-layer network comprises n unique inputs, m nodes in a hidden layer, and a single linear node in an output layer.

18. The method of claim 13, comprising comparing the modified oxygen saturation estimate to a hypoxia oxygen saturation threshold.

19. The method of claim 18, comprising initiating an alarm if the modified oxygen saturation estimate is less than or equal to the hypoxia oxygen saturation threshold.

20. The method of claim 13, wherein the modified oxygen saturation estimate is based at least in part on a combination of the selected oxygen saturation estimate value and a corresponding signal quality metric.

21. The method of claim 13, wherein the modified oxygen saturation estimate has less noise bias than the selected oxygen saturation estimate value.

* * * * *